United States Patent
Wyllie et al.

(10) Patent No.: US 6,814,695 B1
(45) Date of Patent: Nov. 9, 2004

(54) APPARATUS AND METHOD TO ASSIST IN THE DIAGNOSIS OF PREMATURE EJACULATION

(75) Inventors: Michael Wyllie, Kent (GB); Michael O'Leary, Dedham, MA (US)

(73) Assignees: Medicare Management Consultancy Limited, Oxon (GB); The Brigham and Women's Hospital, Inc., Boston, MA (US)

( * ) Notice: Subject to any disclaimer, the term of this patent is extended or adjusted under 35 U.S.C. 154(b) by 1 day.

(21) Appl. No.: 10/130,330

(22) PCT Filed: Nov. 13, 2000

(86) PCT No.: PCT/GB00/04330

§ 371 (c)(1),
(2), (4) Date: Aug. 20, 2002

(87) PCT Pub. No.: WO01/34028

PCT Pub. Date: May 17, 2001

(30) Foreign Application Priority Data

Nov. 11, 1999 (GB) .............................................. 9926617
Aug. 15, 2000 (GB) ............................................. 0019924

(51) Int. Cl.[7] .................................................. A61F 5/00

(52) U.S. Cl. ......................................... 600/38; 600/552

(58) Field of Search ................................ 600/38–41, 4, 600/552; 601/46; 606/201–204

(56) References Cited

U.S. PATENT DOCUMENTS

| 4,407,275 A | 10/1983 | Schroeder ..................... 128/79 |
| 4,848,361 A | 7/1989 | Penney et al. ............... 128/774 |
| 5,931,783 A | 8/1999 | Redano ....................... 600/439 |

FOREIGN PATENT DOCUMENTS

| DE | 2 359 032 | 7/1974 |
| DE | 197 09 324 A | 9/1998 |

*Primary Examiner*—John P. Lacyk
(74) *Attorney, Agent, or Firm*—Drinker Biddle & Reath LLP

(57) ABSTRACT

An apparatus for providing a vibratory stimulus to the penis of a male human comprising a cuff adapted to fit around the penis, which cuff includes one or more vibratory means operable at a pre-determined or variable frequency. A method of measuring premature ejaculation in a male human, said method comprising the steps of: a) positioning a vibratable cuff to the penis of the human; b) providing a vibratory stimulus having either a pre-determined constant frequency or a variable frequency to induce ejaculation; c) measuring the latency time period to ejaculation at said vibratory stimulus and/or the threshold frequency required to induce ejaculation; and d) comparing said latency measurement and/or said threshold frequency to known standard measurements. A method of evaluating a novel potential therapeutic agent for the treatment of premature ejaculation in a male patient. Initial assessment of premature ejaculation can be made as a baseline measurement, and then novel potential therapeutic agents administered to the patients.

17 Claims, 5 Drawing Sheets

APPARATUS AND METHOD TO ASSIST IN THE DIAGNOSIS OF PREMATURE EJACULATION

FIELD OF THE INVENTION

The present invention relates to apparatus and methods to assist in the diagnosis of premature ejaculation, particularly but not exclusively for standardising such diagnosis.

PRIOR ART

In this era of heightened awareness of male and female sexuality, premature ejaculation has been recognised as a very common male sexual health problem, affecting as much as 20–30% of men. Paradoxically, however, it is the disorder for which men are least likely to seek help.

There is no consensus regarding the criteria used to define premature ejaculation. The most recent set of criteria appear in the $4^{th}$ edition of the Diagnostic and Statistical Manual of the American Psychiatric Association. Implicit in the definition is that the disturbance causes marked distress or inter-personal difficulty parameters that can only be assessed qualitatively. No quantifiable endpoints have been agreed upon.

Little is known about the underlying pathophysiology of premature ejaculation as the disorder has been under-researched. There are emerging data to suggest that men with premature ejaculation have hypersensitivity and hyper-excitability of the glans penis and the dorsal nerve; thus there may be both an organic and psychogenic basis for clinical premature ejaculation.

Individual, conjoint and group psychotherapy approaches combined with behavioural strategies such as "stop-start" or "squeeze" techniques have been used in the treatment of premature ejaculation. However long term success is limited. Several devices are also available (see eg U.S. Pat. Nos. 5,468,212 and 5,535,758).

Increasingly, therapeutic agents have been tried in the management of premature ejaculation (see eg U.S. Pat. Nos. 5,587,167, 5,707,999 and 5,863,927). However, in the absence of a detailed understanding of the aetiology of the disorder, the rationale for the selection of the agents evaluated is often unclear. Not surprisingly, success with oral agents has been limited.

It is an object of the present invention to provide apparatus and methods for providing reproducible quantification of premature ejaculation in men.

STATEMENT OF THE INVENTION

According to one aspect of the present invention, there is provided an apparatus to provide a vibratory stimulus to the penis of a male human comprising a cuff able to fit around the penis, which cuff includes one or more vibratory means operable at a pre-determined or variable frequency.

The apparatus of the present invention is able to induce ejaculation in men by the vibratory stimulus applied via a penile cuff. Latency to ejaculation (which is the time period between the start of the stimulus and the ejaculation) can be determined at either a constant vibratory frequency, or at a threshold frequency. The values can be compared to mean values for these parameters obtained historically from normal men, ie those defined as not experiencing clinically significant premature ejaculation. Repeated use of the apparatus and repeated measurements can be made to ensure reproducibility. Desirably the apparatus includes a timing device, preferably an automatic timing device, so that the time to ejaculation is measured.

Advantageously the apparatus further includes control means for controlling the operation of said vibratory means, this control means may be adapted to control the intensity of vibration of said vibratory means. Also, this control means is preferably adapted to control the operation of said vibratory means such that the vibratory means is repeatedly switched alternately on for a first predetermined time period and off for a second predetermined time period.

It is further preferred that the apparatus further includes sensor means adapted to be fitted to the penis. Desirably this sensor means is adapted to detect ejaculation and can be a pulse sensor.

It is further preferred that the apparatus includes means for calculating an event duration comprising the time period between the commencement of stimulation and ejaculation.

It is further preferred that the apparatus further includes data storage means adapted to record at least one of data generated by said sensor means, parameters relating to the operation of said vibratory means and an event duration.

It is further preferred that the apparatus further includes visual display means for displaying at least one of parameters relating to the operation of the apparatus, data and at least one elapsed time period.

It is further preferred that the apparatus further includes interface means whereby the apparatus may communicate with a separate data processing system.

According to a second aspect of the present invention, there is provided a method of measuring premature ejaculation in a male human, said method comprising the steps of:
 a) positioning a vibratable cuff to the penis of the human;
 b) providing a vibratory stimulus having either a pre-determined constant frequency or a variable frequency to induce ejaculation;
 c) measuring the latency time period to ejaculation at said vibratory stimulus and/or the threshold frequency required to induce ejaculation; and
 d) comparing said latency measurement and/or said threshold frequency to known standard measurements.

Advantageously the apparatus according to the invention above described is used to carry out said method.

Such a method can be used to diagnose premature ejaculation. In particular a shorter latency time period and/or lower threshold frequency when compared to standard measurement would be an indication of premature ejaculation condition.

According to a third aspect of the present invention, there is provided a method of evaluating a novel potential therapeutic agent for the treatment of premature ejaculation in a male patient wherein an initial assessment of premature ejaculation can be made as a baseline measurement, and then novel potential therapeutic agents administered to the patients. Thus, the method of the invention comprises the steps of
 A) providing a first measurement of the latency time period to ejaculation and/or the threshold frequency required to induce ejaculation in the patient by:
  (i) positioning a vibratable cuff to the penis of said patient;
  (ii) providing a vibratory stimulus having either a pre-determined constant frequency or the threshold frequency required to induce ejaculation; and
  (iii) measuring the latency time period to ejaculation at either said constant vibratory or at said threshold frequency required to induce ejaculation;

B) administering said agent to said patient;

C) at a pre-determined time, providing second measurement of the latency time period to ejaculation and/or of the threshold frequency required to induce ejaculation as described in the steps (i) to (iii) below; and D) comparing said first and second measurements to determine the efficiency of said agent.

Step C) below may be repeated at different period of time to obtain several measurements. Measurements are advantageously repeated at times relevant to the pharmacokinetic profile of the drug, eg within the period 30 minutes to 24 hours after a single oral dose of the agent under evaluation.

Advantageously the efficiency of said agent is shown by an increase of either the latency time period or the frequency of vibratory stimulus to induce ejaculation of the second measurement when compared to the first measurement. Thus, an agent with clinical potential should either increase ejaculation latency, or the frequency of vibratory stimulus to induce ejaculation, when compared to the baseline measurement, by a defined amount. This could generally be by a minimum of 50%. Efficacy could be measured by the use of placebo agents.

In case also, the method is advantageously carried out using the apparatus of the invention described above.

According to a fourth aspect of the present invention, there is provided a method of evaluating substances for treating premature ejaculation wherein a vibratory frequency and/or period of vibration of a vibratory penile cuff around the penis of a patient is measured at a pre-determined time after administration of a substance, and which frequency and/or period for ejaculation are compared with known standard measurements.

SHORT DESCRIPTION OF THE FIGURES

Embodiments of the invention will now be described, by way of example only, with reference to the accompanying drawings, in which.

PREFERRED EMBODIMENTS OF THE INVENTION

Figure 1:
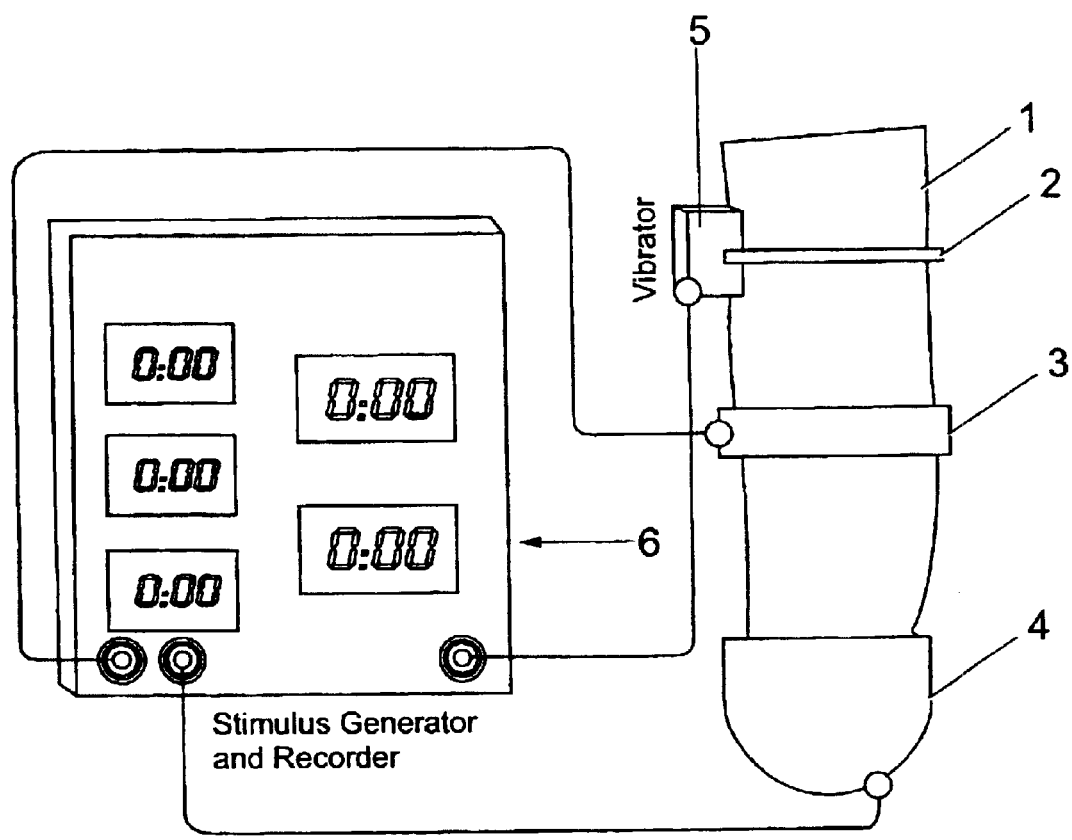
FIG. 1 is a schematic illustration of apparatus in embodying one aspect of the invention.

One embodiment of the invention is illustrated in FIG. 1. Cuffs 2, 3 and 4 are fitted onto the penis 1 of a male human. Cuff 2 provides vibratory stimulation transmitted from at least one vibratory unit 5. Vibratory unit 5 may comprise a DC motor, for example, and is variably controlled by a control unit 6. Cuffs 3 and 4 may be sensors or measurement devices and deliver data to control unit 6 (stimulus generator and recorder). Control unit 6 may include means for controlling the parameters of vibratory stimulus, for measuring time, and for monitoring/recording data signals from sensors 3 and 4, and also for displaying, for example, parameters, time and data.

For the purposes of studying premature ejaculation, the apparatus includes at least one vibrator 5, preferably with controllable intensity (amplitude) and frequency, and at least one sensor for detecting ejaculation, suitably a pulse sensor 3.

Figure 2:
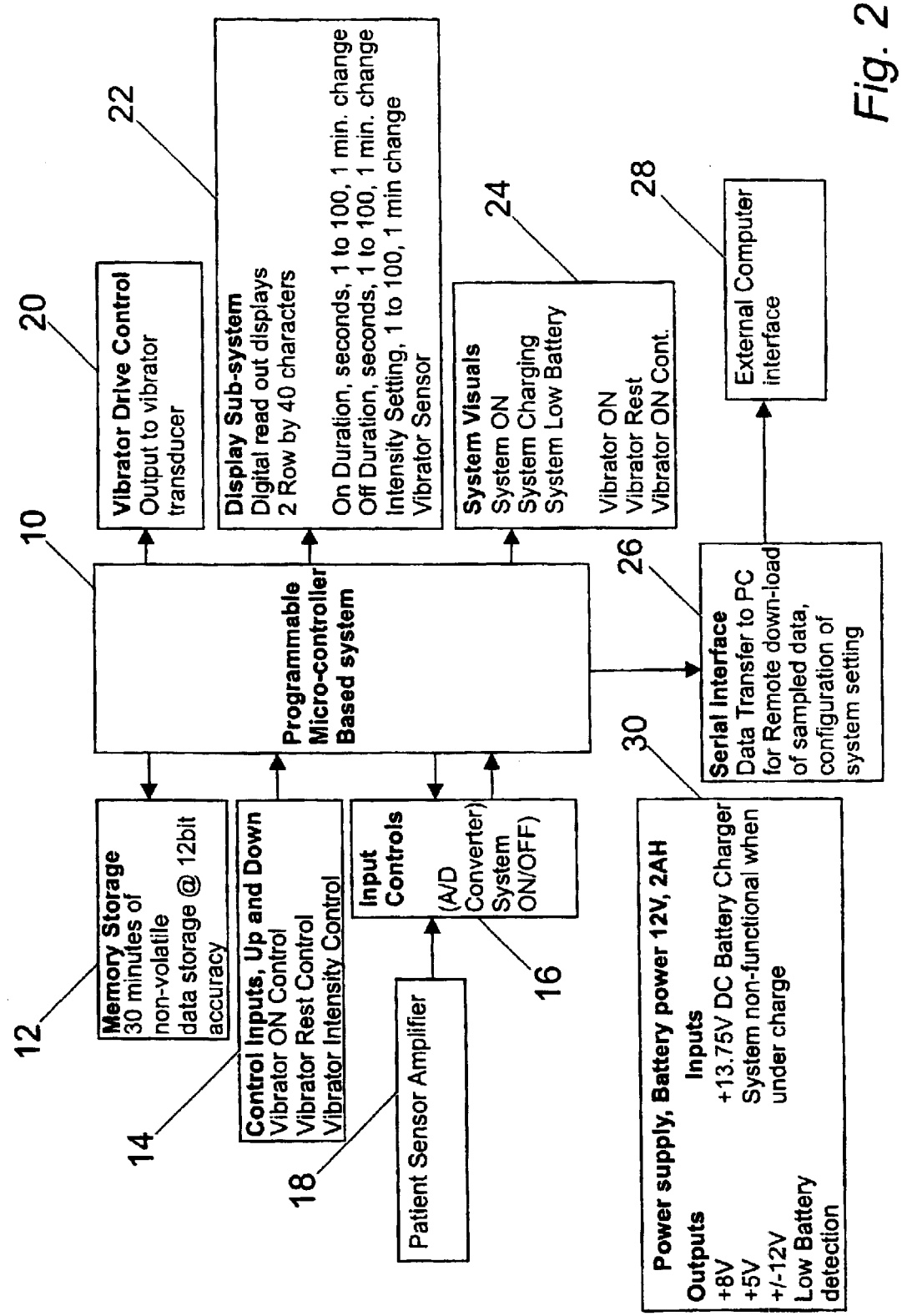
FIG. 2 is a block diagram illustrating a preferred embodiment of apparatus in accordance with the invention.

FIG. 2 is a block diagram illustrating a preferred embodiment of a control unit of apparatus in accordance with the invention, including a programmable microcontroller based system and other subsystems which may be included in the control unit or which may be provided separately therefrom. The microcontroller 10 communicates with other subsystems, as follow:

The microcontroller 10 outputs data to memory storage means 12. The memory storage means 12 is suitably adapted to provide, for example, 30 minutes of nonvolatile data storage at 12-bit accuracy.

The microcontroller 10 receives control inputs from vibrator control means 14, including vibrator ON signals, vibrator OFF ("rest") signals and vibrator intensity signals. The apparatus may be programmed to provide variable stimulus in terms of vibrator intensity (amplitude) and (optionally) frequency, and operational sequences, typically comprising alternating time periods when the vibrator is on and off (e.g. 10 seconds on/10 seconds off, repeated for as long as required).

The microcontroller 10 controls input control means 16 and receives data signals from the input control means 16. The data signals are generated by one or more sensors (including at least the pulse sensor 3 of FIG. 1) and are input to the input control means 16 via a sensor signal amplifier 18. The input control means includes analog-digital (A/D) converter means for digitising signals received from the amplifier 18. The microcontroller 10 controls the operation of the input control means 16.

The microcontroller 10 outputs control signals to vibrator drive control means 20, determined by the vibrator control means 14, which in turn generates output signals to drive the vibrator transducer 5.

The microcontroller 10 controls a display sub-system 22, which includes digital display means, suitably a 2-row by 40 character display. The display means will typically display the selected stimulus parameters, namely: the ON duration, suitably in the range 1 to 100 seconds, variable in increments of one second; the OFF duration, again suitably in the range 1 to 100 seconds, variable in increments of one second; and the intensity setting, suitably variable on an arbitrary scale of 1 to 100, variable in increments of 1 unit. The display suitably also displays the elapsed time since the beginning of the stimulus ("event durations"), typically in seconds or minutes and seconds.

The microcontroller 10 also controls additional visual status indicators 24 (e.g. LEDs or the like): e.g. system ON, system charging, battery low, vibrator ON, vibrator rest, vibrator on continuously.

The micro-controller 10 is preferably also connected to a serial interface, enabling data transfer to an external computer interface 28, for downloading sampled data and system settings to a separate computer or other data processing/storage system.

The apparatus is suitably operated by rechargeable battery power (power supply 30).

Figure 3:
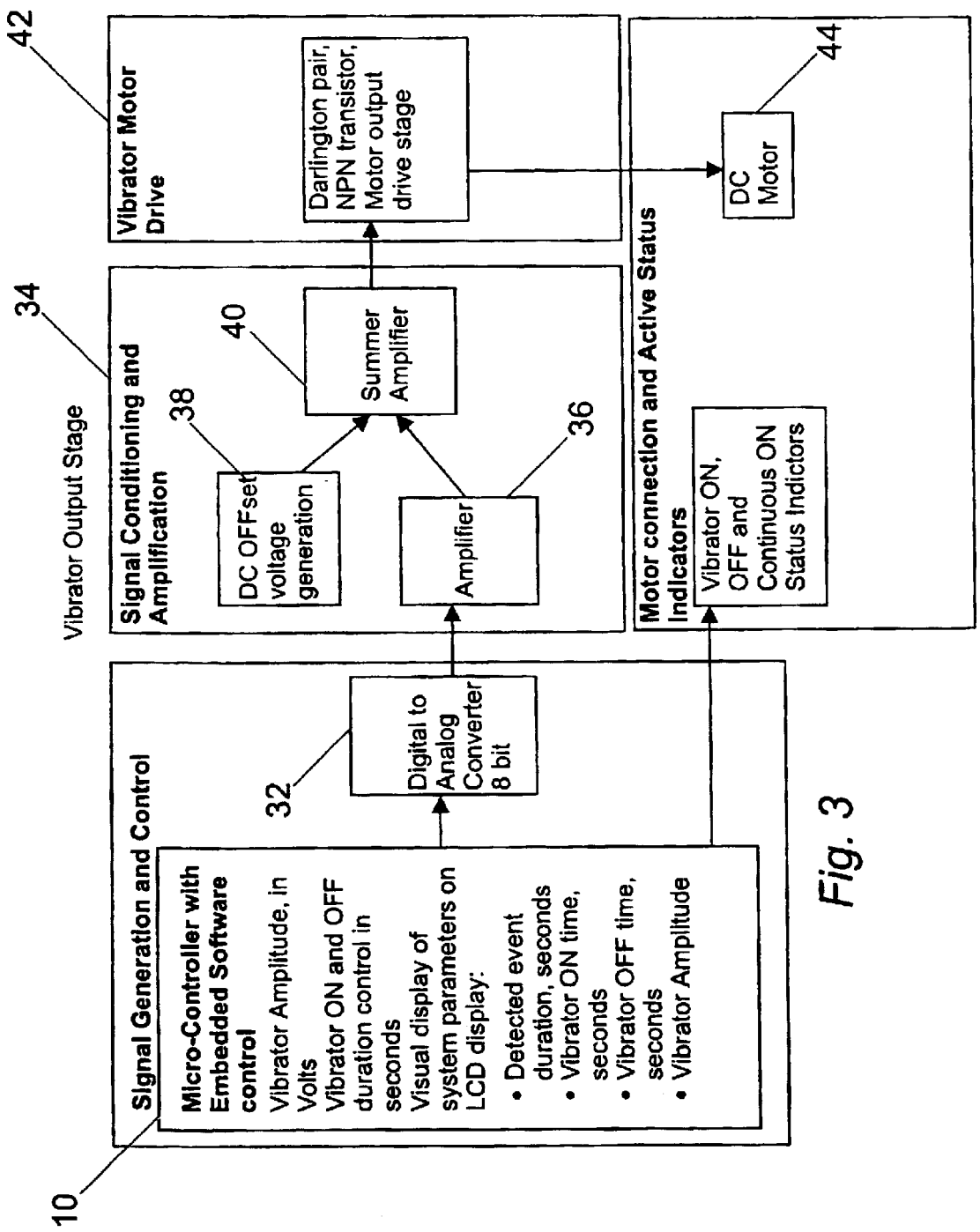
FIG. 3 is a block diagram illustrating an example of a vibrator output stage of the apparatus of FIG. 2.

FIG. 3 illustrates the vibrator output stage of FIG. 2 in more detail. The microcontroller 10 and its associated vibrator control inputs determine the required vibrator parameters: amplitude and ON and OFF periods, with appropriate outputs to the visual display and status indicators. For the purposes of driving the vibrator, the digitally encoded parameters are converted to analog signals by digital-analog (D/A) converter 32. The analog signals output by D/A converter 32 are processed by a signal conditioning and amplification stage 34. For example, the analog signal is amplified by amplifier 36 and the output from amplifier 36 is added to a DC offset voltage (determined by offset voltage voltage generator 38) by summer amplifier 40. The output from the signal conditioning and amplification stage 34 is input to a vibrator motor drive stage 42, which in turn drives the DC vibrator motor 44.

Figure 4:
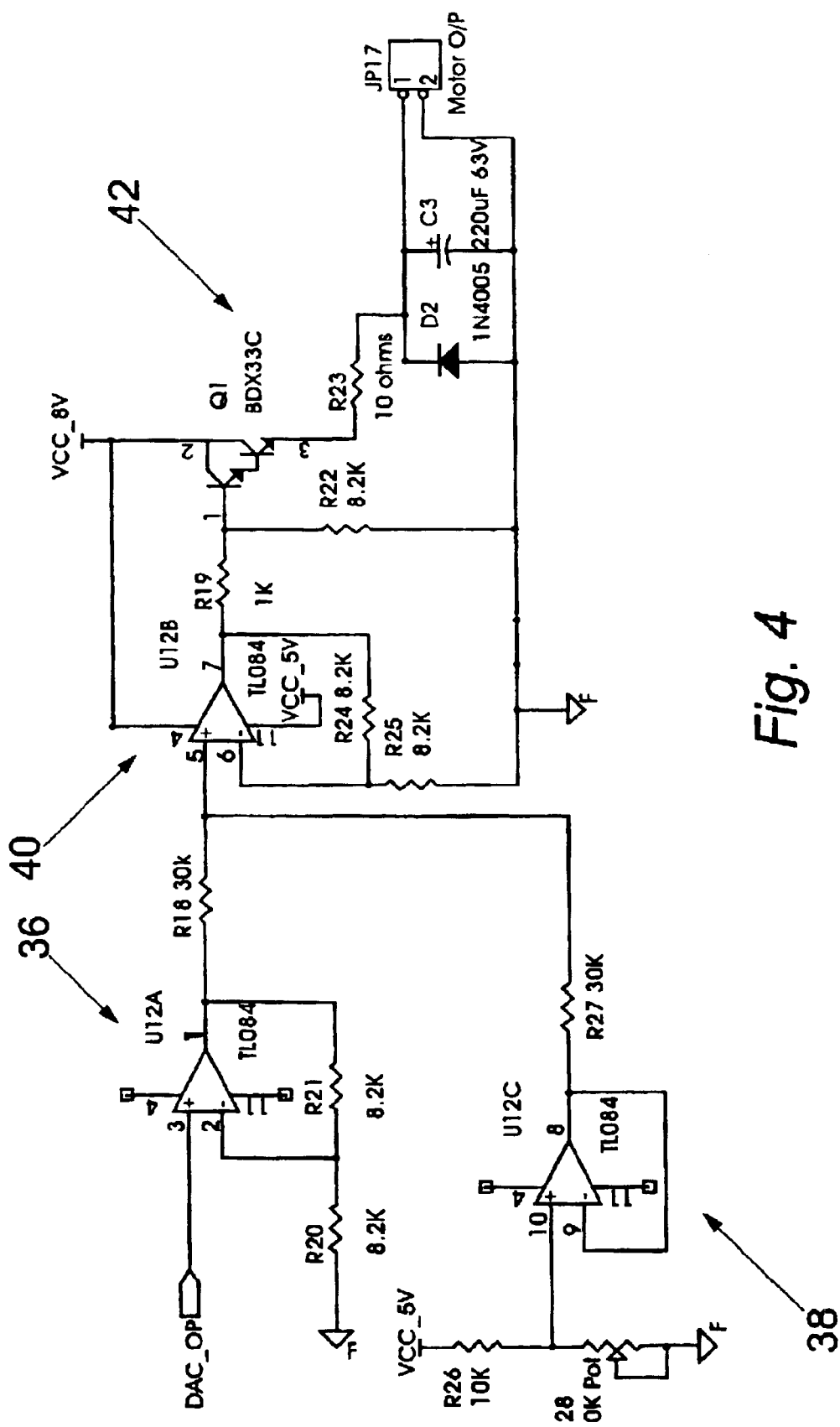
FIG. 4 is a circuit diagram of an example of a vibrator output stage as illustrated in FIG. 3.

FIG. 4 is a circuit diagram of the vibrator output stage corresponding to blocks 34 and 42 of FIG. 3.

Figure 5:
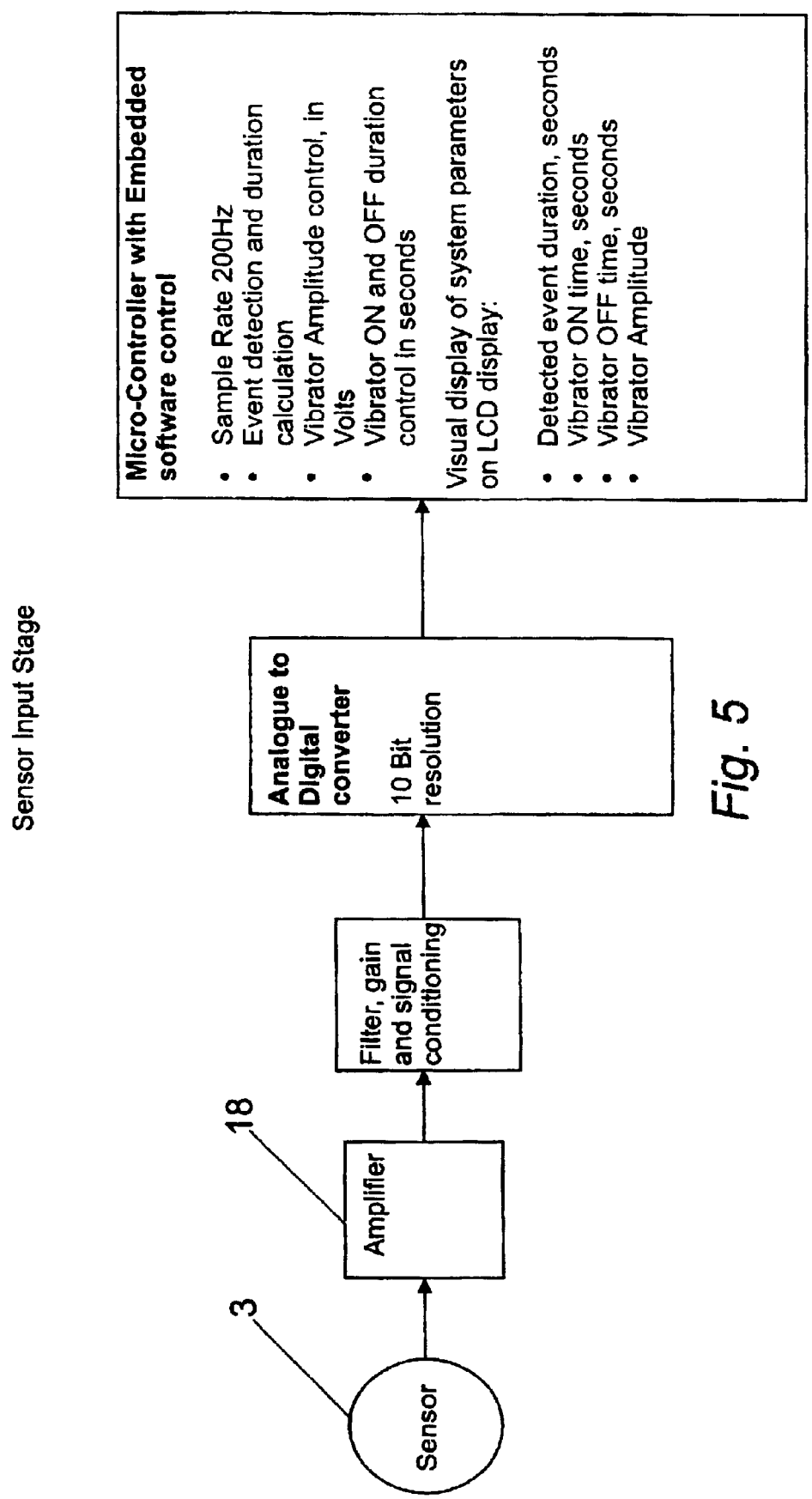
FIG. 5 is a block diagram illustrating an example of a sensor output stage of the apparatus of FIG. 2.

FIG. 5 illustrates the sensor input stage of FIG. 2 in more detail. The output from the pulse sensor 3 is input to the sensor amplifier 18. The output from the amplifier 18 is input to a filter, gain and signal conditioning stage 46 of the input control means 16, the output of which is applied to D/A converter 48, and the output from D/A converter 48 is input to the microcontroller 10 as previously described. The analog sensor data is sampled at a suitable frequency, such as 200 Hz. Ejaculation may be detected on the basis of detected pulse strength, from which the event duration may be determined.

The apparatus of the present invention (for example as illustrated in FIGS. 1 to 5) was applied to a number of male humans not generally considered to have premature ejaculation. A number of measurements were taken for time for ejaculation with the penile cuff apparatus operated at a constant frequency, and a number of measurements were taken of the threshold frequency to induce ejaculation following the application of increased frequency to the penile cuff apparatus.

The penile cuff apparatus was then applied to a number of other male human patients and their period for inducing ejaculation at a constant frequency, and/or their threshold frequency for inducing ejaculation were measured. These measurements were then compared to the measurements of the normal male humans, and those measurements outside standard deviation were diagnosed as patients having premature ejaculation.

The invention provides a method of evaluation and diagnosis of premature ejaculation and the identification of novel treatments for this disorder. It should be understood that this invention is not limited to the particular embodiments shown and described herein, but various changes and modifications can be made without departing from the spirit and scope of this novel concept as defined herein.

What is claimed is:

1. Apparatus for providing a vibratory stimulus to the penis of a male human comprising:
    a cuff adapted to fit around the penis, which cuff includes one or more vibratory means operable at a pre-determined or variable frequency; and
    sensor means adapted to be fitted to the penis and to detect ejaculation and calculate an event duration comprising the time period between the commencement of stimulation and ejaculation.

2. Apparatus as claimed in claim 1, further including control means for controlling the operation of said vibratory means.

3. Apparatus as claimed in claim 2, wherein said control means is adapted to control the intensity of vibration of said vibratory means.

4. Apparatus as claimed in claim 2, wherein said control means is further adapted to control the operation of said vibratory means such that the vibratory means is repeatedly switched alternately on for a first predetermined time period and off for a second predetermined time period.

5. Apparatus as claimed in claim 1, wherein said sensor means is a pulse sensor.

6. Apparatus as claimed in claim 1, further including data storage means adapted to record at least one of data generated by said sensor means, parameters relating to the operation of said vibratory means, and an event duration.

7. Apparatus as claimed in claim 1, further including visual display means for displaying at least one of parameters relating to the operation of the apparatus, data, and at least one elapsed time period.

8. Apparatus as claimed in claim 1, further including interface means whereby the apparatus may communicate with a separate data processing system.

9. A method of measuring premature ejaculation in a male human, said method comprising the steps of:
    a) positioning a vibratable cuff to the penis of the human;
    b) providing a vibratory stimulus having either a pre-determined constant frequency or a variable frequency to induce ejaculation;
    c) measuring the latency time period to ejaculation at said vibratory stimulus and/or the threshold frequency required to induce ejaculation; and
    d) comparing said latency measurement and/or said threshold frequency to known standard measurements.

10. The method of claim 9, comprising the step of positioning the apparatus as claimed in claim 1 to the penis of the human.

11. The method of claim 9, comprising the step of comparing said latency measurement and/or said threshold frequency to known standard measurements to diagnose premature ejaculation.

12. The method of claim 11, wherein a shorter latency time period and/or lower threshold frequency when compared to standard measurement is an indication of premature ejaculation condition.

13. A method of evaluating a novel potential therapeutic agent for the treatment of premature ejaculation in a male patient said method comprising the steps of:
    (a) providing a first measurement of the latency time period to ejaculation and/or the threshold frequency required to induce ejaculation in said patient by:
        i) positioning a vibratable cuff to the penis of said patient;
        ii) providing a vibratory stimulus having either a pre-determined constant frequency or the threshold frequency required to induce ejaculation; and
        (iii) measuring the latency to ejaculation at either said constant vibratory or at said threshold frequency required to induce ejaculation;
    (b) administering said agent to said patient;
    (c) at a pre-determined time providing second measurement of the latency time period to ejaculation and/or of the threshold frequency required to induce ejaculation as described in the steps (i) to (iii) above; and
    (d) comparing said first and second measurements to determine the efficiency of said agent.

14. The method of claim 13, wherein step (c) is repeated at different periods of time to obtain several measurements.

15. The method of claim 13, wherein efficiency of said agent is shown by an increase of either the latency time period or the frequency of vibratory stimulus to induce ejaculation of the second measurement when compared to the first measurement.

16. The method of claim 15, wherein said increase is at least of 50%.

17. The method of claim 13, comprising the step of positioning the apparatus as claimed in claim 1 to the penis of the patient.

* * * * *